United States Patent
Hsu

[11] Patent Number: 5,754,389
[45] Date of Patent: May 19, 1998

[54] STRUCTURE FOR A STATIC ELECTRICITY GROUNDING STRAP

[76] Inventor: Shih-Min Hsu, Taipei Hsien, Taiwan

[21] Appl. No.: 757,732

[22] Filed: Nov. 26, 1996

[51] Int. Cl.$^6$ ...................................................... H05F 3/02
[52] U.S. Cl. ............................................ 361/220; 361/212
[58] Field of Search ......................................... 361/212, 213, 361/214, 220, 221, 222

[56] References Cited

U.S. PATENT DOCUMENTS

| | | | |
|---|---|---|---|
| 4,398,277 | 8/1983 | Christiansen et al. | 361/220 |
| 4,577,256 | 3/1986 | Breidegam | 361/220 |
| 4,639,825 | 1/1987 | Breidegam | 361/212 |
| 4,662,695 | 5/1987 | Gordon et al. | 361/220 |
| 4,782,425 | 11/1988 | Breidegam | 361/212 |
| 4,845,585 | 7/1989 | Weiss | 361/220 |
| 4,998,178 | 3/1991 | Weiss | 361/220 |
| 5,018,044 | 5/1991 | Weiss | 361/220 |
| 5,036,423 | 7/1991 | Williams . | |
| 5,548,469 | 8/1996 | Adams | 361/220 |
| 5,568,351 | 10/1996 | West et al. . | |

FOREIGN PATENT DOCUMENTS 258386  3/1983  China .

Primary Examiner—Fritz Fleming
Attorney, Agent, or Firm—Finnegan, Henderson, Farabow, Garrett & Dunner, L.L.P.

[57] ABSTRACT

A static electricity grounding strap for connecting a person to electrical ground comprising a clasp body having two clasping means to fasten a strap belt of conductive materials. In one embodiment of the present invention, the clasping means is made of non-conductive material. The electrical connection path is conducted via a single conductive plate from the strap belt, a fitting means and a grounding cord to ground. The conductive plate can also be divided into two conductive section separated by a non-conductive partition to provide a dual-loop grounding paths. In another embodiment, the clasping means is made of conductive materials and no additional conductive plates are needed.

10 Claims, 6 Drawing Sheets

STRUCTURE FOR A STATIC ELECTRICITY GROUNDING STRAP

The present invention relates to an improved structure for a static electricity grounding strap that can be conveniently and easily changed without additional tools.

BACKGROUND OF THE INVENTION

Static electricity grounding straps have been widely used in the electronic element manufacturing process, especially in the semiconductor manufacturing process to prevent electronic elements from being damaged by static electric potential or surge voltage. In operation, the static electricity grounding straps are wound around a person's wrist with conductive strips thereof being in contact with the person's body and conductive wires are connected with conductive strips to the ground so that the static electric potential generated in operation is wicked from the person's body to ground via the conductive wire.

One of the conventional grounding strap structures is disclosed in Chinese Patent No. UM-104,700 which is published on 21 Sep. 1995 and is owned by the inventor of the subject invention. As shown in FIG. 1, the grounding strap belt 1 made of woven conductive materials is fastened to a clasp body 2. The clasp body 2 has a through slot 21 on one side thereof for fixedly mounting one end of the strap belt 1 and a recess 22 on the other side thereof. A fastening means 23 is pivotably mounted on one end of the recess 22 so as to adjustably mount the other end of the strap belt 1. The recess 22 further has a through hole 221 on the bottom. Two conductive strips 222 and 223 are provided, each having a through hole and is in turn attached to the through hole 221 on the recess 22, whereby a plug means 224 can penetrate through the holes to electrically connect the two conductive strips 222 and 223. The plug means 224 is also engageable with a grounding cord (not shown) so that when in use, the conductive strips, in contact with a person, conduct the static electricity away from the person's body to ground so as to prevent the electronic elements from being damaged.

The above structure, however, is complex enough where the cost to manufacture such a strap may be high as compared to other types of grounding straps. It is therefore desirable that a novel structure of the strap is provided which can be easily assembled and detached to save labor and cost.

SUMMARY OF THE INVENTION

The object of the present invention is to provide a static electricity grounding strap, of which the structure is simplified so that the strap can be easily assembled. In addition, the strap is adjustable and detachable in operation.

According to one embodiment of the present invention, the clasp body is made of non-conductive material which has two recesses on two ends thereof for placing the strap belt. Two clasping means of nonconductive material are pivotably mounted to the ends of the body so that the strap belt can be fixed adjustably to the recesses through clasping means. One of the recesses has an opening for providing a conductive strip to pass through and attach to therein. The conductive strip is a single strip for providing a single-loop electric conductive path.

According to an alternative embodiment of the present invention, the strap also can be used to provide dual-loop electric conductive paths. To achieve such a purpose, the two recesses are separated by a partition and each of the recesses has an opening for receiving a conductive strip respectively.

In a further embodiment of the present invention, the clasping means are used to be base plates which can be made of conductive material which are pivotably mounted to the partition on the back of the clasp body so as to be in contact with the wearer of the strap. Since the clasping means are conductive, they can replace the separate conductive strips in the above embodiments in addition to clasp the strap belt, to provide the electrical path for the static voltage. Thus, the structure of the strap can be further simplified.

These and other objects, advantages and features of the present invention will be more fully understood and appreciated by reference to the written specification.

DETAILED DESCRIPTION OF THE PREFERRED EMBODIMENT

Figure 1:
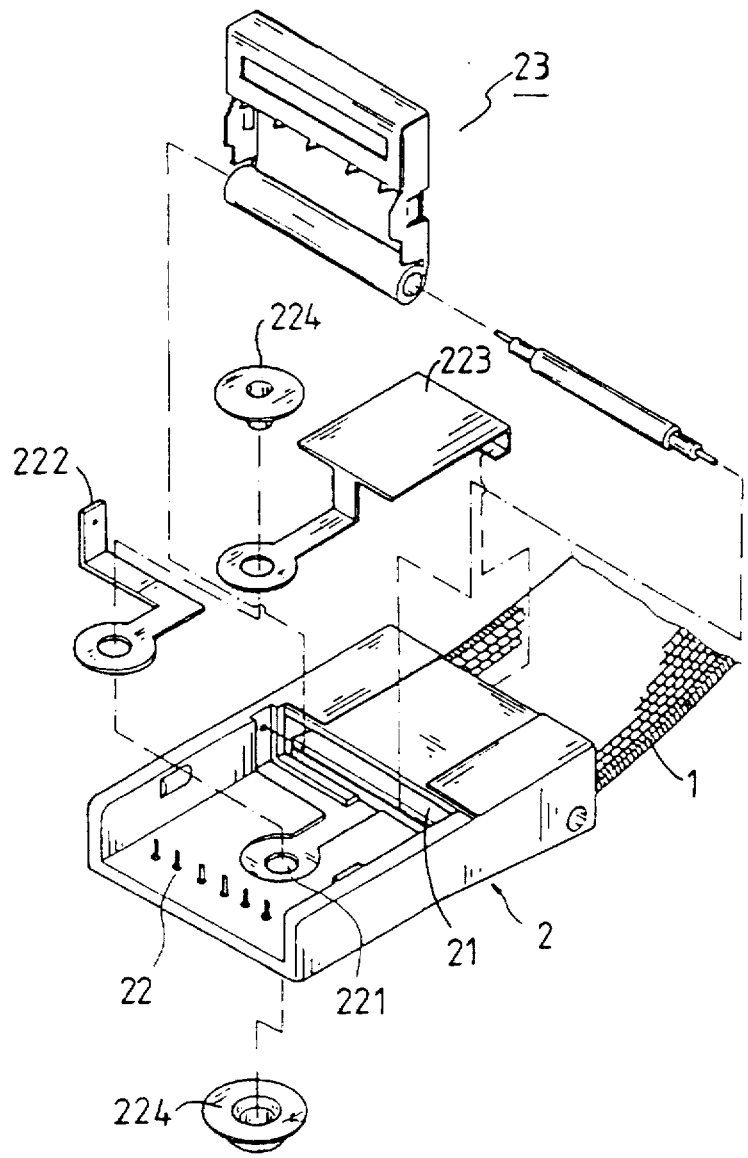
FIG. 1 shows an exploded perspective view of a conventional static electricity grounding strap.
Figure 2A:
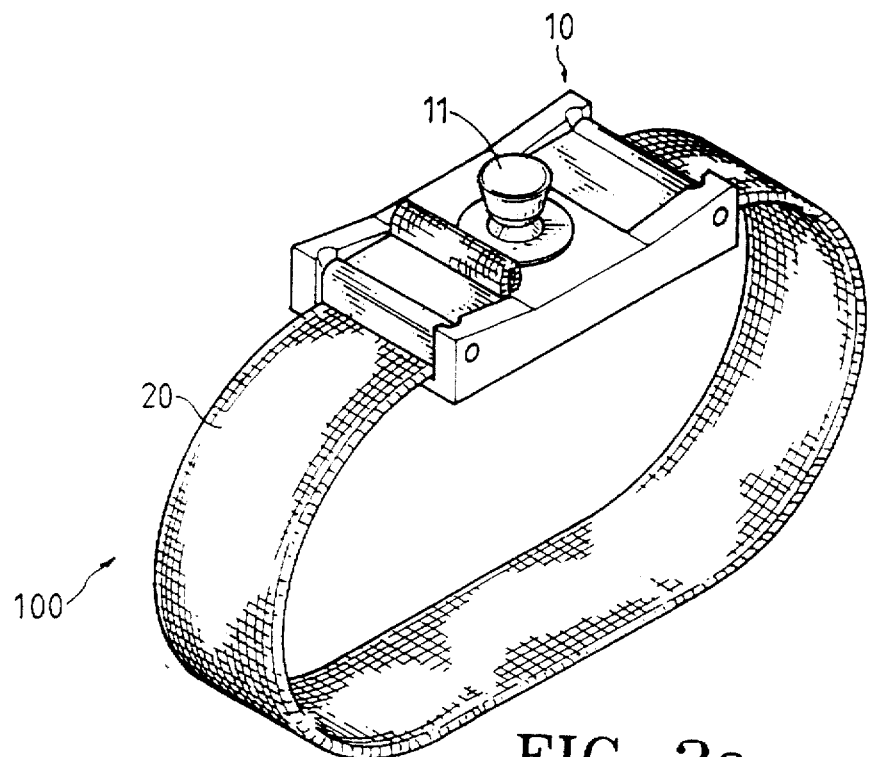
FIG. 2a shows a perspective view of a single-loop static electricity grounding strap in accordance with one embodiment of the present invention.
Figure 2B:
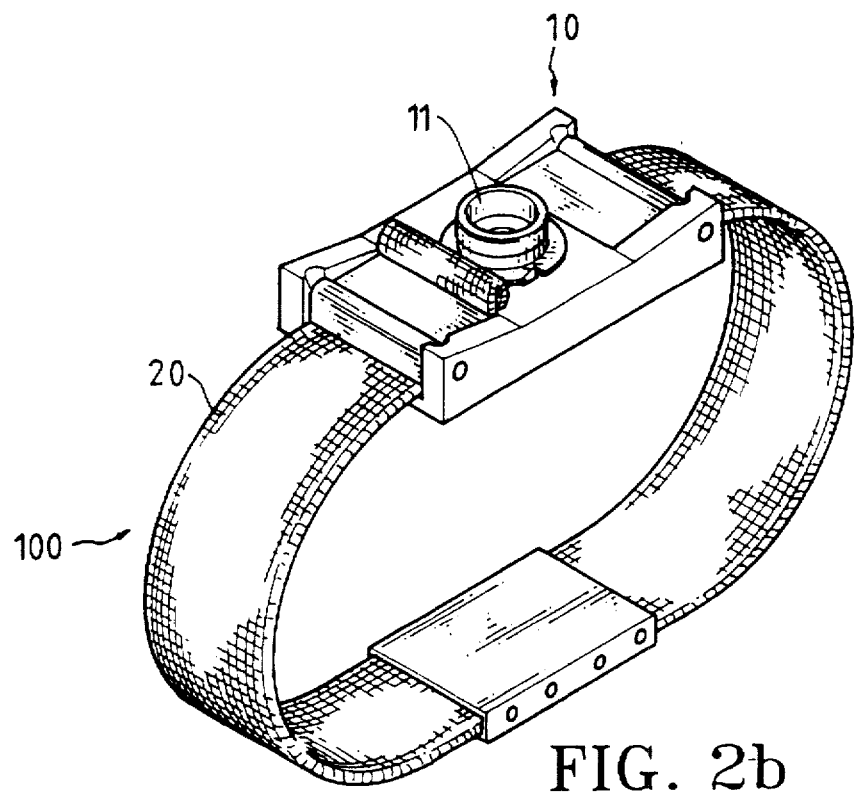
FIG. 2b shows a perspective view of a dual-loop static electricity grounding strap in accordance with one embodiment of the present invention.

FIGS. 2a and 2b respectively represent a perspective view of a static electricity grounding strap 100 in accordance with the present invention, in which FIG. 2a is used for a single loop and FIG. 2b is for a dual-loop. The static electricity grounding strap 100 mainly comprises a clasp body 10 and a strap belt 20 attached to the clasp body 10 wherein the strap belt 20 may be made out of electrical conductive woven material or metallic link to provide an electrical loop path for the electrostatic voltage.

Figure 3:
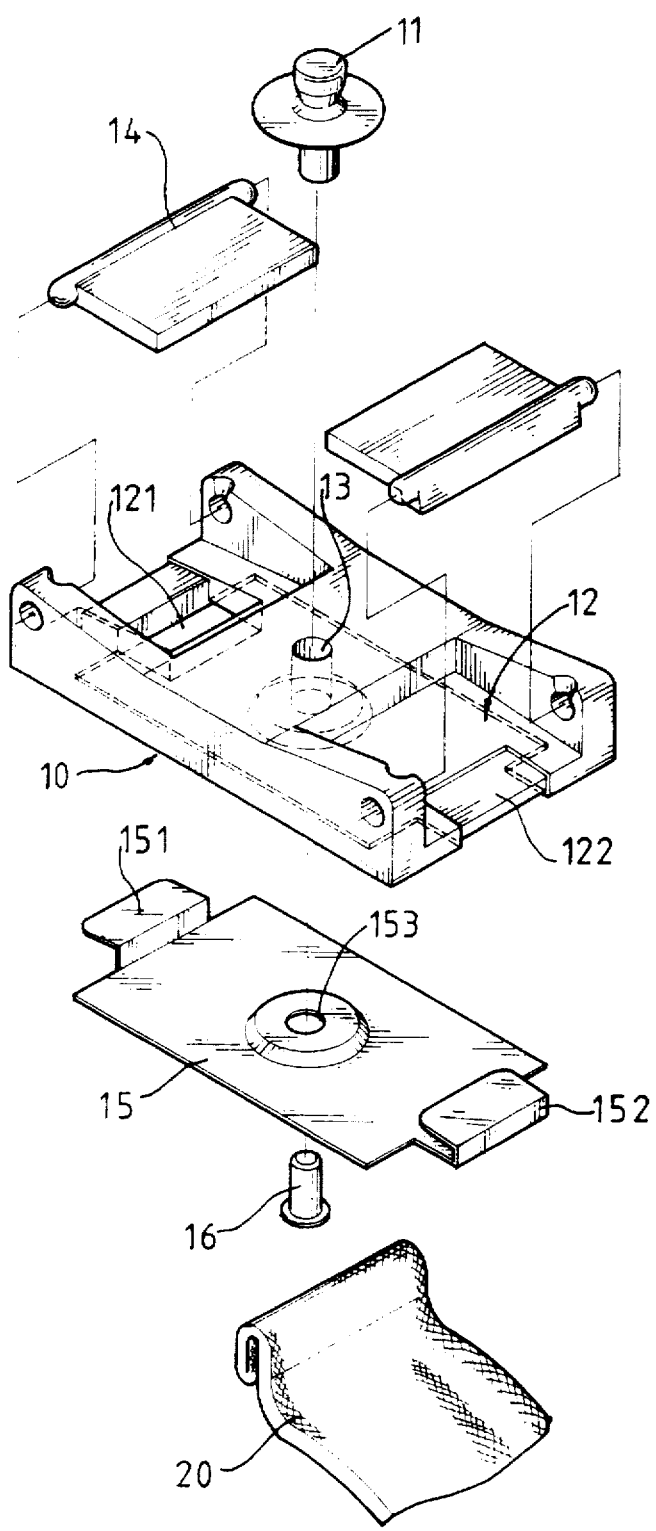
FIG. 3 shows an exploded view of a single-loop static electricity grounding strap in accordance with the present invention.

FIG. 3 shows an exploded view in accordance with another embodiment of the present invention. As shown in the figure, the clasp body 10 is made out of a non-conductive material having a through hole 13 at the center of the body 10 for receiving a fitting means 11 and two recesses 12 at two opposing ends on the top surface thereof for receiving the strap belt 20, each recess 12 being large enough to receive a clasping means 14. The clasping means 14 are made out of non-conductive material which are pivotably connected on both ends of the clasp body 10, respectively for adjustably securing the strap belt 20.

A conductive plate 15 having an integral tab 151 extending upwardly and outwardly on one end thereof and an integral engaging member 152 on the other end thereof is mounted to the back of the clasp body 10. To receive the conductive plate 15, one recess 12 of the clasp body 12 has an opening 121 and the other recess 12 has a step portion 122 on the outward end thereof. The opening 121 is large enough so that the tab 151 of the conductive plate 15 can penetrate therethrough and can be engaged by the engaging member 152 of the conductive plate 15. When mounting the conductive plate 15 to the clasp body 10, the tab 151 is firstly passed through the opening 121 from the back of the clasp body 10 and then slid laterally so that the tab 151 abuts the body 10 and the engaging member 152 engages with the step portion 122 and then fixed on said body 10.

The fitting means 11 engaged into the through hole 13 of the clasp body 10 is electrically coupled to the conductive plate 15 and is provided for connecting a grounding cord (not shown). To make an electrical connection, the conductive plate 15 still has a through hole 153 on the corresponding position to the through hole 13 of the clasp body 10 to allow a conductive fastening means 16 (e.g., a rivet) to fasten the conductive plate 15, the clasp body 10 and the fitting means 11 together. In usage, the connective plate 15 is in contact with the wearer's wrist so that the electrostatic voltage generated by the wearer can be directed from the conductive plate 15, the fitting means 11 and the grounding cord to ground.

The embodiment shown in FIG. 3 illustrates a single-loop grounding strap in accordance with the present invention. The grounding strap of FIG. 3 can be alternatively changed to be used in dual-loop application without departing from the spirit of the present invention. The dual-loop grounding strap in accordance with the present invention is shown as FIG. 4.

Figure 4:
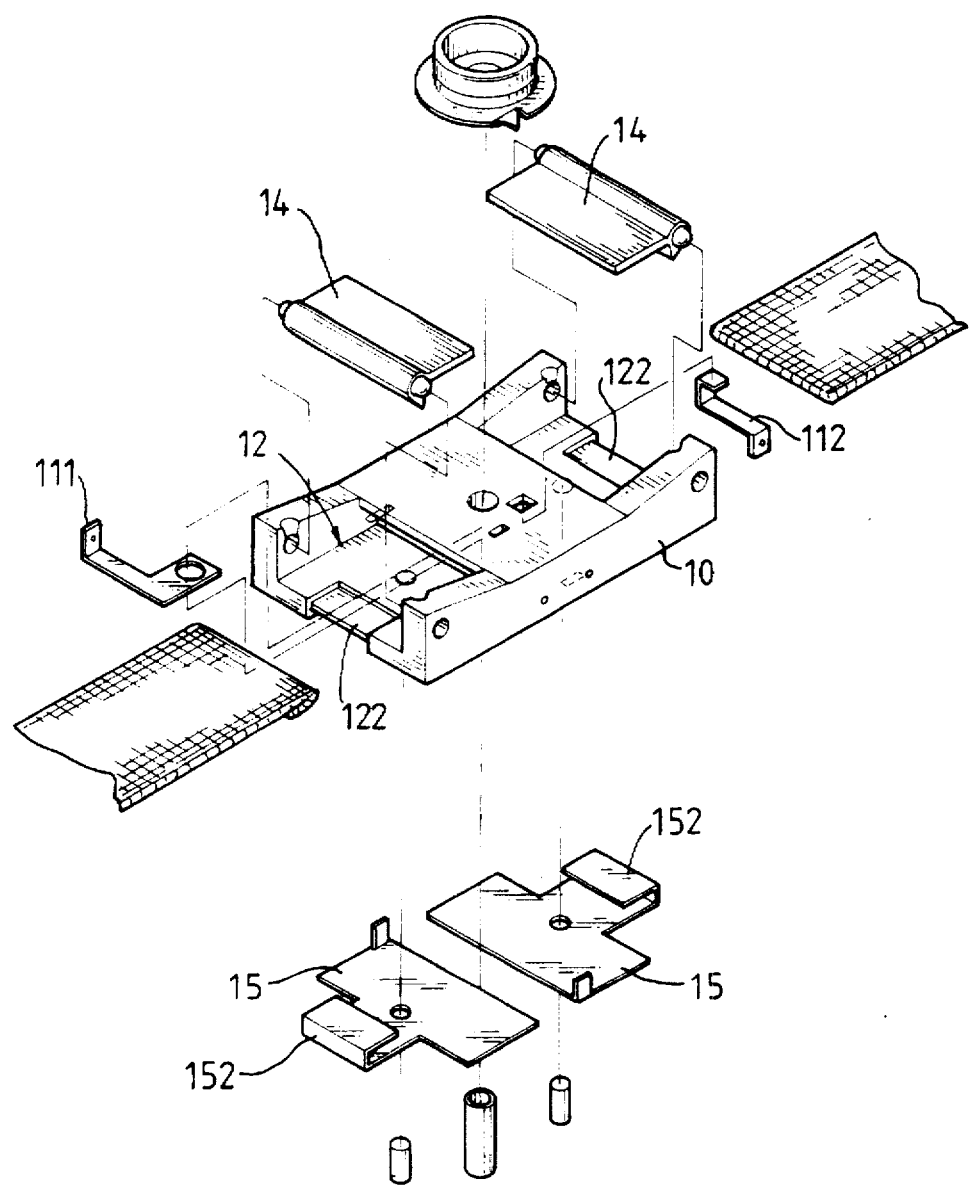
FIG. 4 shows an exploded view of a dual-loop static electricity grounding strap in accordance with a second embodiment of the present invention.

As shown in FIG. 4, the clasping means 14 are pivotably mounted on the recesses 12 of the clasp body 10 in the same manner as mentioned in above except that there are two conductive plates 15 respectively having an engaging member 152 for engaging with the clasp body 10 from the ends of the back surface of the clasp body 10. The clasp body 10 further has a non-conductive integral partition 101 (shown on FIG. 6) on the center of the back surface thereof to insulate the two conductive plates 15. In the embodiment of FIG. 4, each of the recesses 12 has a step portion 122 on the outer end thereof for engaging with the engaging member 152 of the conductive plate 15. In the dual-loop grounding strap, the fitting means 11 has extended two conductive legs 111 and 112 to respectively connect electrically with the conductive plates 15 to provide two separate current paths.

Figure 5:
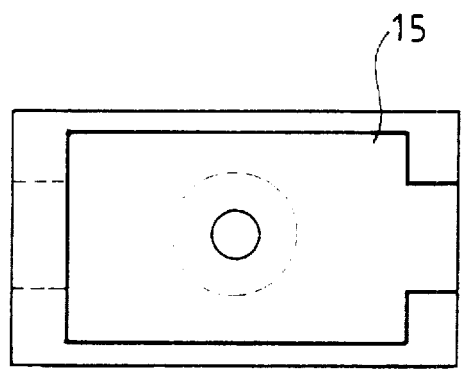
FIGS. 5 and 6 show the back views of the single-loop and dual-loop static electricity grounding straps of FIGS. 3 and 4, respectively.
Figure 6:
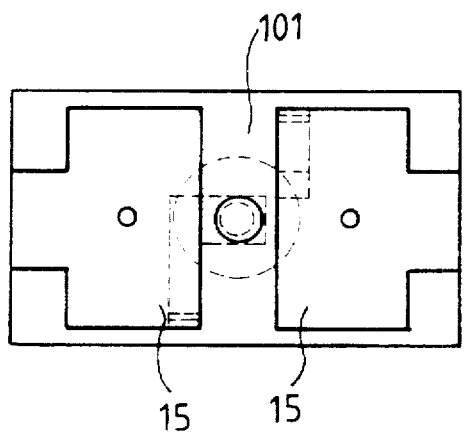

FIGS. 5 and 6 respectively show the back view of the single-loop and dual-loop grounding straps of FIGS. 3 and 4. As can be seen from the figures, the clasp body 10 must have a partition 101 in the dual-loop grounding strap to insulate the conductive plates 15 so that two separate current paths can be provided.

Figure 7:
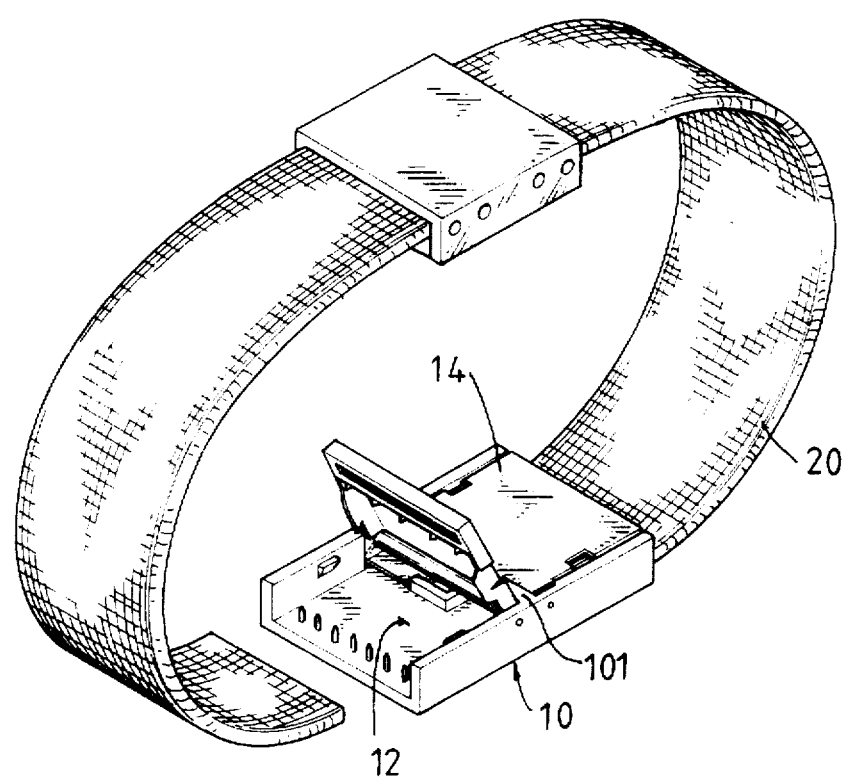
FIG. 7 shows an exploded view of a dual-loop static electricity grounding strap in accordance with the third embodiment of the present invention.

The dual-loop electrostatic grounding strap in accordance with the present invention can also be amended, changed or simplified without departing from the spirit and scope of the present invention. FIG. 7 shows another embodiment of the present invention in which the conductive strips 15 are omitted.

As shown in FIG. 7, the clasp body 10 is also made out of non-conductive material with a partition 101 integrally provided on the back surface thereof. On the back surface of the body 10, there are two recesses 12 separated by the partition 101. The clasp body 10 further has an opening (not shown) on the top face thereof for receiving a fitting means. As mentioned in the above embodiment, to provide a dual-loop grounding strap, two electrical connections must be established between the fitting means and the strap belt 10. Two clasping means 14 are pivotably connected on each side of the partition 101 for clasping the strap belt 20. To replace the conductive strips 15, the clasping means 14 in accordance with the embodiment should be made out of conductive material so that the clasping means 14 can conduct the electrostatic current paths between the strap belt 20 and the fitting means in addition to clasp the strap belt. It is clear from the figure that the construction of the clasp body is simplified and therefore the cost and labor can be further reduced.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A static electricity grounding strap comprising:
   a strap belt;
   a clasp body made of non-conductive material having at least two clasping means on respective ends of said clasp body for clasping said strap belt, comprising:
   two recesses on two opposing ends of a top surface of said clasp body, each recess being large enough to receive said clasping means; one of said recesses having an opening at a distance away from an outer end of said one recess and the other of said recesses having a step portion on an outer end of said other recess;
   a single conductive plate having a tab extending upwardly and outwardly from one end of said conductive plate and an engaging member on the other end of said conductive plate; said opening of said one recess being large enough to allow said tab of said conductive plate to penetrate therethrough and slide therein; said conductive plate being attached to said clasp body from the back surface of said clasp body with said tab penetrating through said opening and sliding in said opening to be mounted on said one recess and said engaging member being engaged with said step portion of said other recess; and
   a fitting means being mounted on the top surface of said clasp body electrically coupled to said conductive plate and said strap belt for receiving a grounding cord.

2. A grounding strap as claimed in claim 1, wherein said clasping means are made of non-conductive material and are pivotably connected with said recesses.

3. A grounding strap as claimed in claim 1, wherein said strap belt is made of conductive material.

4. A static electricity grounding strap comprising:
   a strap belt;
   a clasp body made of non-conductive materials having at least two clasping means on respective ends of said clasp body for clasping said strap belt, comprising:
   two recesses on two opposing ends of a top surface of said clasp body, each recess being large enough to receive said clasping means;
   a partition on a back surface of said clasp body to electrically insulate said recesses;
   two conductive plates each having an engaging member on one end thereof for engaging with each of said recesses; said conductive plates being attached to said clasp body from the back surface of said clasp body with said partition separating said respective conductive plates; and
   a fitting means for receiving a grounding cord; said fitting means being mounted on the top surface of said clasp body which has two conductive legs to electrically connect with said conductive plate when said conductive plates are attached to said clasp body.

5. A grounding strap as claimed in claim 4, wherein said clasping means are made of non-conductive material and are pivotably connected with said recesses.

6. A grounding strap as claim in claim 4, wherein said strap belt is made of conductive material.

7. A static electricity grounding strap, comprising:

a strap belt;

a clasp body made of non-conductive material having at least two clasping means on respective ends of said clasp body for clasping said strap belt, comprising:
two recesses on two opposing ends of a back surface of said clasp body, each recess being large enough to receive said clasping means;
a partition on a back surface of said clasp body to electrically insulate said two recesses; and a fitting means for receiving a grounding cord being mounted on the top surface of said clasp body;

wherein said clasping means are made of conductive materials and being pivotably mounted on respective sides of said partition for clasping said strap belt to make electrical connection with said strap belt; and said fitting means has two conductive legs which is electrically connect with said clasping means and said strap belt.

8. A grounding strap as claimed in claim 7, whrerin said strap belt is made of conductive material.

9. A grounding strap as claimed in claim 7, wherein said strap belt is stretchable woven.

10. A grounding strap as claimed in claim 7, wherein said strap belt is metallic.

* * * * *